United States Patent [19]

Bistrian et al.

[11] Patent Number: 4,906,664

[45] Date of Patent: Mar. 6, 1990

[54] NUTRITIONAL SUPPLEMENT FOR TREATMENT OF CANCER CACHEXIA

[75] Inventors: Bruce R. Bistrian, Ipswich; Vigen R. Babayan, Waban; George L. Blackburn, Jamaica Plain, all of Mass.

[73] Assignee: New England Deaconess Hospital Corporation, Boston, Mass.

[21] Appl. No.: 144,930

[22] Filed: Jan. 15, 1988

[51] Int. Cl.[4] .............................................. A61K 31/23
[52] U.S. Cl. .................................................... 514/552
[58] Field of Search .................. 514/552, 557, 558, 560

[56] References Cited

U.S. PATENT DOCUMENTS 4,528,197  7/1985  Blackburn ........................... 514/552
4,607,052  8/1986  Mendy et al. ....................... 514/547
4,703,062  10/1987 Blackburn et al. ................... 514/552

OTHER PUBLICATIONS

Mok et al., (1984) Metabolism; 33: 910–915.

Handbook of Physics and Chemistry 57th ed. CRC Press pp. D216–217, Robert Weast editor.

"Medium-chain triglycerides: an update," Back and Babayan, Amer. J. of Clin. Nut., 38: Nov. 1982, pp. 950–962.

"Improved Protein Kinetics and Albumin Synthesis by Branched Chain Amino Acid-Enriched total Parenteral Nutrition in Caner Cachexia," Tayek et al., Cancer, 58: No. 1, Jul. 1, 1986.

"Some Practical and Theoretic Concepts in the Nutritional Assessment of the Cancer Patient," Bistrian, Cancer, 58: No. 8, Oct. 15, 1986.

*Primary Examiner*—Jerome D. Goldberg
*Assistant Examiner*—Henley, VIII Raymond J.
*Attorney, Agent, or Firm*—Lahive & Cockfield

[57] ABSTRACT

A method of treating cancer cachexia syndrome has been discovered. Total parenteral nutrition using structured lipids in place of long chain fatty acids as the primary lipid source provides improvements in nitrogens balance, plasma serum albumin levels, and glucose clearance rate.

4 Claims, 2 Drawing Sheets

NUTRITIONAL SUPPLEMENT FOR TREATMENT OF CANCER CACHEXIA

BACKGROUND OF THE INVENTION

The present invention relates to nutritional support for patients suffering from cancer cachexia. More particularly, the present invention concerns a method for providing total parenteral nutrition for cancer cachexia patients which yields improved nitrogen balance, improved plasma albumin levels, and decreased glucose clearance as compared with conventional total parenteral nutrition.

Cancer cachexia syndrome is characterized by reduced dietary intake and progressive weight loss, primarily, but not exclusively, through the loss of skeletal muscle and adipose tissue. Cancer cachexia syndrome is found in association with a number of conditions, e.g., after surgery or radiotherapy for malignancy, or mechanical obstruction of the gastrointestinal tract as in esophageal cancer.

Use of total parenteral nutrition can ameliorate the problem of reduced dietary caloric intake in cancer cachexia patients but the use of conventional total parenteral nutrition formulas appears to replete fat stores rather than saving and/or restoring lean muscle tissue. These conventional total parenteral nutrition formulas consists primarily of either carbohydrates, e.g., glucose, or long chain triglycerides (LCT), e.g., safflower and/or soybean oil. However, carbohydrate diets can lead to insulin problems while LCT diets lead to fat deposition in the liver, impair leukocyte chemotaxis and random migration, and interfere with the function of reticuloendothelial system function.

In order to overcome these problems, medium chain triglycerides (MCT) have been tried as a source of total parenteral nutrition in certain conditions, e.g., liver disfunction. MCT's are formed from saturated fatty acids with chain lengths of 6-12 carbons, primarily 8-10 carbons, linked to a glycerol backbone. MCT's have a unique metabolism which has advantages for total parenteral nutrition; they are rapidly absorbed by the body through the portal system without initial intestinal hydrolysis. In contrast, LCT's require initial hydrolysis and absorption by the lymphatic system before they can be utilized as an energy source. Moreover, MCT's cause fewer fat deposits in the liver and are much more rapidly used as an energy substrate. Because of this, enteral and parenteral applications for MCT diets have been proposed. See Bach and Babyan in "Medium-Chain Triglycerides: Update," Am.J.Clin. Nutrition 36, pp. 950-962, November 1982.

However, there have been problems reported with the use of high levels of MCT's in diet. Intravenous administration of large quantities of MCT's in dogs or rats has produced somnolence, vomiting, coma and death. Because the MCT's are digested in the liver, liver disfunction patients may also not be good candidates for MCT therapy. To counter act these potential problems, as well as fulfilling the need for certain amounts of $\omega 6$ fatty acids, e.g., linoleic acid, required for proper metabolic functioning, physical mixtures of LCT's and MCT's, as well as structured lipids having medium chain fatty acids and long chain fatty acids on the same glycerol backbone, have been used. In fact, both physical mixtures and structured lipids have been used as total enteral or parenteral nutrition for hypercatabolic patients. See U.S. Pat. No. 4,528,197, assigned to KabiVitrum, Inc.; DeMichele et al., "Effect of Total Enteral Nutrition with Structured Lipids of Protein Metabolism in Thermally Injured Rats," Fed.Proc. 46:1086 (1987); and U.S. Pat. No. 4,703,062, assigned to Baxter-Travenol, Inc.

Although there are some similarities between hypercatabolic states and cancer cachexia, they are clinically distinct. For example, hypercatabolic patients uniformly show increased losses of body protein, as reflected in urinary nitrogen excretion. In contrast, patients with cancer cachexia often show a positive rather than negative nitrogen balance. See Bistrian, "Some Practical and Theoretical Concepts in Nutritional Assessment of the Cancer Patient," CANCER 58(8):1863-1866 (1986). Therefore, treatments effective for hypercatabolic states may not be appropriate for cancer cachexia.

Accordingly, an object of the invention is to provide a method for supplying nutrition to cancer cachexia patients which spares lean muscle and adipose tissue.

Another object of the invention is to provide total parenteral nutrition for cancer cachexia patients.

A further object of the invention is to provide a method of improving nitrogen balance, plasma albumin levels, and glucose clearance rates in cancer cachexia patients.

These and other objects and features of the invention will be further described in the description and the drawings.

SUMMARY OF THE INVENTION

Figure 1:
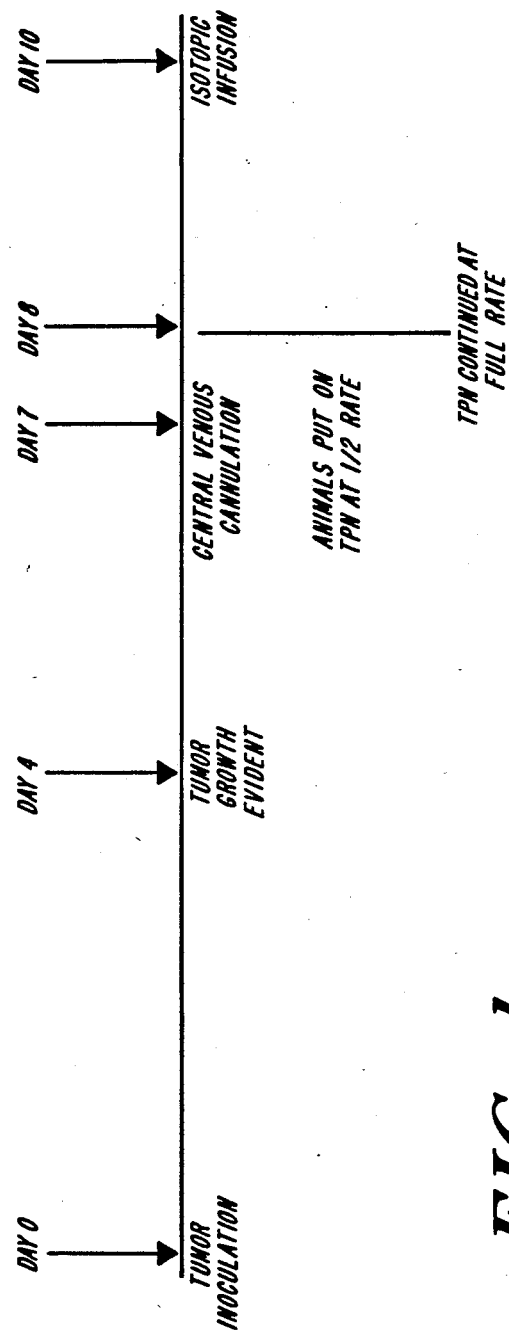
FIG. 1 is a schematic illustration of the experimental design used in the Example.

The present invention features a method of providing nutritional support to patients suffering from cancer cachexia. This nutritional support is based on the use of structured lipids as the primary lipid source in the diet.

The method of the invention for providing nutritional support to patients suffering from cancer cachexia has the step of parenteral administration of a diet containing an effective amount of a structured lipid as the primary lipid source. This structured lipid provides a large proportion of the calories in the diet. The structured lipid used in the invention has the structure

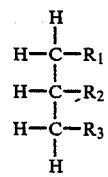

where at least one of $R_1$, $R_2$, and $R_3$ is a medium chain fatty acid or a derivative thereof and the others of $R_1$, $R_2$, and $R_3$ are selected from a group consisting of medium chain fatty acids, long chain fatty acids, and derivatives thereof. Preferably, the structured lipid is a blend of randomly esterified structured lipids such that the ratio of long chain fatty acids to medium chain fatty acids is approximately 1:1. The long chain fatty acids associated with the structured lipid should be primarily $\omega 3$ and $\omega 6$ fatty acids, with at least sufficient $\omega 6$, preferably in the form of linoleic acid, to provide adequate lipid metabolism, e.g., prostaglandin synthesis. The classifications ω3 and ω6 are based on the location of the double bond closest to the methyl end of the fatty acid; that is, if the closest double bond is between the third and fourth carbon atoms from the methyl groups, the molecules are ω3 fatty acids, while if the double bond is located between the sixth and seventh carbon atoms, the molecules are classified as ω5 fatty acids. Man and other mammals can desaturate or elongate the fatty acids chains but cannot interconvert fatty acids from one family to another. The structured lipids of the invention can be hydrolysed into their component fatty acids.

The method of the invention will include total parental nutrition of cancer cachexia patients. This total parenteral nutrition includes carbohydrates, e.g., glucose, and amino acids as well as the lipid component.

DETAILED DESCRIPTION OF THE INVENTION

The method of the invention for treating cancer cachexia patients is based on the beneficial effect of using structured lipids to ease some of the nutritional problems associated with the cancer. The diet does not have any direct effect on the spread or growth of the cancer, e.g., there is no difference in the tumor growth rate. Instead, the invention uses parenteral administration of the structured lipids to provide improved nutritional benefits which may allow a patient to thrive during treatment of the cancer with radiotherapy or chemotherapy.

Structured lipids do not provide the same benefits if administered enterally rather than parenterally. See Swanson et al., "Sturctured Lipid (SL) as a Component of Total Enteral Nutrition (TEN) in Rats Bearing Yoshida Sarcoma (YS), [Cite], which shows that the use of structured lipids in total enteral nutrition does not change nitrogen balance or provide significant beneficial effects in rats having Yoshida sarcoma induced cancer cachexia.

The effect of structured lipid of parenteral nutrition on cancer cachexia patients can best be illustrated by the following Example.

EXAMPLE

A. Experimental Procedure

FIG. 1 illustrates the experimental design of the Example. Male Sprague-Dawley rats weighing approximately 45 gm were broken into two groups; one group was inoculated with $10^7$ cells of viable Yoshida sarcoma into the subcutaneous area of the right flank, and the other group received an identical injection of sterile saline. The animals were weighed, returned to their cages, and allowed to continue standard laboratory chow and tap water for seven days. The rats bearing the rapidly growing tumors (Yoshida sarcoma) had diminished appetites and when re-weighed at day 7 were significantly lighter than the nontumor-bearing animals, indicating their cachectic state.

At day 7, all of the rats were anaesthetized and a silastic catheter was inserted through the internal jugular vein. The animals were randomly divided into four groups and were administered total parenteral nutrition through the catheter.

Table I gives the dietary composition in terms amino acids, glucose and lipids administered to all the animals.

TABLE I

DIETARY COMPOSITION

| Group | Amino Acids kcal/kg.BW | Glucose kcal kg.BW | Lipid kcal/kg.BW | Total kcal/kg.BW |
|---|---|---|---|---|
| LCT | 50 (22%) | 85 (39%) | 85 (39%) | 220 |
| SL | 50 (22%) | 85 (39%) | 85 (39%) | 220 |

| Additives per 1000 ml: | |
|---|---|
| NaCl | 30 mEq |
| NaAC | 30 mEq |
| KCl | 30 mEq |
| KAc | 25 mEq |
| KPhos | 16 mEq |
| Ca + Gluconate | 8.4 mEq |
| MgSO4 | 8.0 mEq |
| Trace minerals | 10.2 mEq |

0.5 ml of MVC 9 + 3 vitamins and 0.25 ml of choline chloride (30% w/v) were added per 100 ml of hyperal solution.

The control (nontumor and tumor) groups received the lipid in the form of long chain triglycerides (Liposyn II, a 50:50% mixture of safflower and soybean oil, Abbott Laboratories, North Chicago, Illinois) and the test groups received a structured lipid having equal amounts of medium chain fatty acids and long chain fatty acids randomly esterified on a glycerol backbone (KabiVitrum, Inc., Stockholm, Sweden). The diets were administered at half the planned rate the first night (day seven-eight) to allow for adaption to the glucose and fat and then at full caloric intake thereafter. Holter pumps (Critikon, Inc., Tampa, Fla.) were used for infusion of the diet through the catheter and the infusion rate was adjusted so each animal received 220 calories/kg body weight/day with 2 gm amino nitrogen/kg body weight/day. Twenty-four hours urine sample was collected for nitrogen balance determination.

On day 10, $(1-^{14}C)$-1-leucine (50mCi/mmol, ICN, Irvine, Calif.) and 6-$^3$H-glucose (Amersham International, Inc., Amersham, U.K.) were added to the diets and a four hours constant infusion was conducted to investigate protein and glucose kinetics. Each animal received 1.5 uCi/hour of leucine and 14 uCi/hour of glucose at a rate of 1.25 cc/hour.

After the infusion, the animals were sacrificed by decapitation, the blood was collected in heparinized tubes, and placed on ice. Plasma was separated by centrifugation and stored at $-25°$ C. until the time of analysis. The body was quickly dissected and the liver, tumor and portions of the abdominus rectus muscle removed. The muscle, tumor and liver were weighed and stored.

Plasma glucose specific activity was determined by deproteinizing the samples using $Ba(OH)_2$ and $ZnSO_4$ and the glucose was separated on a cation/anion exchange column. Glucose flux, or total appearance was calculated by dividing the infusion rate of labelled glucose by the plasma glucose specific activity. Endogenous appearance was calculated by subtracting the rate of glucose infusion from the rate of glucose flux. Glucose clearance rate was calculated by dividing the glucose flux by the plasma glucose concentration.

Albumin concentration was determined by transferring 10 ml of plasma into test tubes containing 6 ml of a bromcresol green solution and distilled water, 1:5 v/v. The samples were analyzed spectrophotometrically at a wavelength of 630 nm. Albumin concentration were determined by linear regression of known standards and unknowns were determined from the regression line.

Rates of whole body leucine appearance and oxidation, as well as the percentage of leucine oxidation, synthesis, breakdown and balance were estimated by assuming that a plateau labelling (steady state) of the plasma component was achieved when the specific activity maximum was reached in the expired breath. The protein fractional synthetic rates in the liver and abdominus rectus muscle were estimated as a difference between the tumor protein synthesis, measured isotopically, and the tumor growth. Estimates of fractional tumor growth were derived from tumor volume measurements on days 7 and 10. Tumor volumes were estimated by measurements of tumor length, width and depth. These measurements bear a close relationship to tumor weight.

B. Experimental Results

The experiments reported in this Example show that certain factors were not affected by diet. First, there was no significant difference in weight change between the animals receiving the structured lipid or LCT supplements. Second, there was no significant difference between the tumor growth rates between the structured lipid-infused and LCT-infused animals. In fact, a separate group of tumor bearing rats, which did not undergo jugular catheterization and were allowed to consume laboratory chow in place of the lipid diets, had not significant difference in tumor growth rate, showing that total parenteral nutrition does not significantly affect tumor growth. Third, the percentage of protein in the tumor, and the tumor protein fractional synthetic and breakdown rates were substantially the same, showing no significant differences in tumor growth or kinetics due to the administration of structured lipids or LCT-enriched total parenteral nutrition. In fact, whole-body protein kinetics showed no significant differences due to the effect of diet manipulation or even tumor presence.

There were changes, however, in liver kinetics. Table II illustrates liver and muscle kinetics for the infused animals.

TABLE II

| | LIVER AND MUSCLE KINETICS | | | |
|---|---|---|---|---|
| | T SL | T LCT | NT SL | NT LCT |
| *Liver Wt (gs) | 6.0 ± 0.8 | 6.0 ± 0.6 | 5.4 ± 0.5 | 5.7 ± 0.4 |
| **Liver Wt/ Body Wt (%) | 4.3 ± 0.3 | 4.5 ± 0.4 | 3.9 ± 0.2 | 4.2 ± 0.2 |
| *Liver FSR (%/day) | 18.6 ± 4.9 | 23.9 ± 12.0 | 14.9 ± 7.0 | 14.4 ± 5.5 |
| **Muscle FSR(%/day) | 1.6 ± 0.5 | 2.4 ± 0.5 | 2.8 ± 0.5 | 3.4 ± 1.2 |
| Muscle % Protein(%) | 19.7 ± 4.6 | 20.0 ± 2.1 | 19.2 ± 5.6 | 20.2 ± 4.0 |

Mean ± STD
*p < 0.05 tumor vs. nontumor
**p < 0.05 tumor vs. nontumor and SL vs. LCT The four groups of animals are the tumor carrying rats infused with structured lipid (T SL), the tumor bearing rats infused with long chain triglyceride (T LCT), nontumor-bearing rats receiving structured lipid (NT SL) and nontumor-bearing rats infused with long chain triglycerides (NT LCT). Although there were significant differences in the liver size between the tumor-bearing and nontumor-bearing rats, there was no significant difference in gross liver weight between the rats receiving the structured lipid and LCT diets. However, when liver weight was calculated as a percentage of body weight, the liver was significantly smaller in the structured lipid infused rats than the LCT infused rats. This is due to the larger body weight of the animals fed the structured lipid diet, perhaps reflecting the improved nitrogen balance.

Table II also illustrates the muscle kinetics, based on the testing of the abdominus rectus muscle. Although there is an increase in the fractional synthetic rate in the abdominus rectus muscle by administering the LCT rather than the structured lipid diet, the percentage of protein in the muscle was substantially identical.

The most significant differences in results caused by administration of the structured lipid diet appear in the plasma albumin levels, nitrogen balance, and glucose clearance kinetics. Table III illustrates the plasma albumin levels for all four groups.

TABLE III

| PLASMA ALBUMIN | |
|---|---|
| | **Plasma Albumin Levels (gm/dL) |
| TUMOR SL | 2.76 ± 0.28 |
| TUMOR LCT | 2.48 ± 0.19 |
| NONTUMOR SL | 3.20 ± 0.21 |
| NONTUMOR LCT | 2.98 ± 0.18 |

Mean ± STD
**p < 0.05 tumor vs. nontumor and SL vs. LCT

The plasma albumin levels were significantly lower in all the tumor-bearing animals than in the nontumor animals but the albumin levels were higher in the tumor bearing animals receiving the structured lipid infusion as compared with those infused with LCT. Since hypoalbuminemia in tumor-bearing animals is normally an indication that the tumor growth occurs at the expense of visceral protein synthesis, the improvement may be an important indication of saving of body protein by diet. Although the basis for this increase in plasma albumin levels is not clear, synthetic activity of protein has been found to be more sensitive to nutrition than increased catabolic rate so it is likely that the increase in plasma albumin caused by the nutritional change reflects extra synthesis of secretory proteins rather than a decrease in protein catabolism.

Table IV illustrates glucose kinetics and their dependence on diet. Although there are differences between the tumor and nontumor states in terms of glucose flux and appearance, the only significant difference caused by diet is in glucose clearance where the use of the structured lipid in place of the long chain triglycerides reduces clearance rate.

TABLE IV

| | GLUCOSE KINETICS | | | |
|---|---|---|---|---|
| | PLASMA CONCENTRATION (mg/dL) | *FLUX (umol/hr/ 100 g BW) | *APPEARANCE (umol/hr/ 100 g BW) | **CLEARANCE (ml/hr/ 100 g BW) |
| TUMOR SL | 173 ± 72 | 756 ± 144 | 176 ± 110 | 89 ± 31 |
| TUMOR LCT | 149 ± 46 | 897 ± 277 | 284 ± 266 | 110 ± 13 |

TABLE IV-continued

| | GLUCOSE KINETICS | | | |
|---|---|---|---|---|
| | PLASMA CONCENTRATION (mg/dL) | *FLUX (umol/hr/ 100 g BW) | *APPEARANCE (umol/hr/ 100 g BW) | **CLEARANCE (ml/hr/ 100 g BW) |
| NONTUMOR SL | 138 ± 18 | 575 ± 113 | 2 ± 104 | 78 ± 19 |
| NONTUMOR LCT | 124 ± 10 | 656 ± 69 | 79 ± 48 | 96 ± 14 |

Mean ± STD
*p < 0.05 tumor vs. nontumor
**p < 0.05 SL vs. LCT

Since the glucose clearance rate gives an estimate of the ability of the tissues to take up glucose, glucose clearance was significantly lower in all animals receiving the structured lipid total parenteral nutrition, this decrease in glucose clearance with the structured lipid-enriched infusion suggests some resistance to glucose uptake. In fact, this result might imply that structured triglycerides are a preferred metabolic fuel as compared with glucose molecules.

Figure 2:
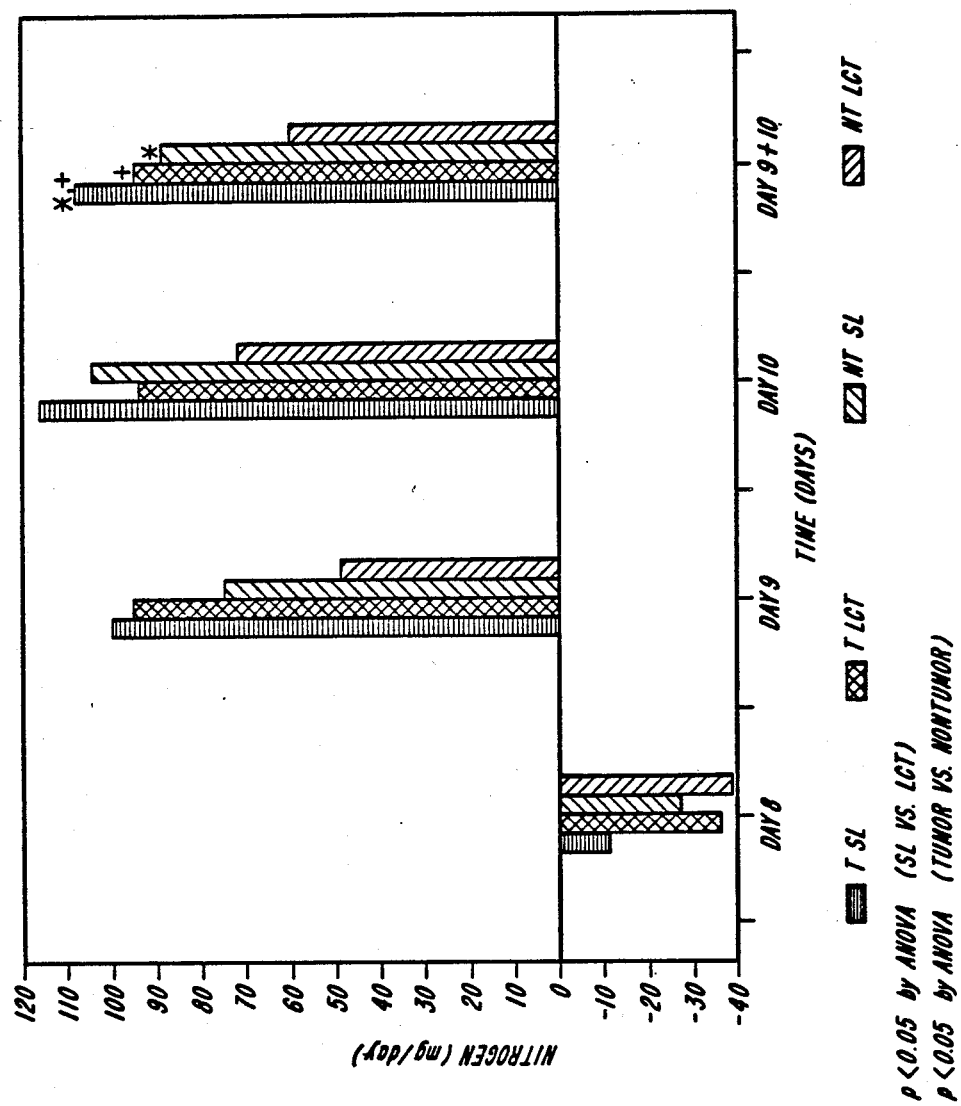
FIG. 2 illustrates the cumulative nitrogen balance as described in the Example.

Cumulative nitrogen balance also increased significantly using the structured lipid infusion as compared with the long chain triglyceride infusion. FIG. 2 illustrates the cumulative nitrogen balance at days 8, 9, 10 and the combination of days 10 and 11. At day 8, all of the animals had a net negative nitrogen balance while on day 9, all show a positive cumulative balance. The tumor-bearing animals had a higher nitrogen balance at all times; however, the use of the structured lipid supplement improves the cumulative nitrogen balance even further, yielding a statistically significant improvement. The improvement in cumulative nitrogen balance suggests that the structured lipid diet is uniquely able to promote nitrogen retention is comparison to other lipid calorie sources in a tumor model. Since nitrogen retention is a measure of protein and/or amino acid sparing, the improved nitrogen balance is a significant advantage achieved by using a structured lipid in place of long chain triglycerides.

In contrast to the improvement in nitrogen balance using parenteral administration of structured lipid, an enteral administration does not yield this same positive effect. In fact, there is no significant difference in nitrogen balance between animals receiving structured lipids or long chain triglycerides when the nutrition is delivered enterally rather than parenterally. This is in sharp contrast to the use of the structured lipid in hypercatabolic states where improved nitrogen balance is observed with either enteral or parenteral administration.

The foregoing Example is purely illustrative and is not intended to be a limitation on the invention. Those skilled in the art can determine other modifications on the formulations used herein. Such modification are included within the following claims.

What is claimed is:

1. A method for providing nutritional support to patients suffering from cancer cachexia comprising the step of parenteral administration of a diet containing an effective amount of a structured lipid as its primary lipid calorie source, said structured lipid having the structure

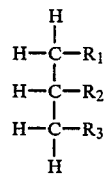

where at least one of $R_1$, $R_2$, and $R_3$ is a medium chain fatty acid, at least one of $R_1$, $R_2$, and $R_2$ is a $\omega 3$ long chain fatty acid, and the other of $R_1$, $R_2$, and $R_3$ is selected from the group consisting of medium chain fatty acids, long chain fatty acids,.

2. The method of claim 1 wherein said diet further comprises nutritionally sufficient sources of carbohydrates and amino acids.

3. The method of claim 1 wherein said diet comprises total parenteral nutrition.

4. The method of claim 1 wherein said structured lipid, upon hydrolysis, yields approximately equal amounts of medium chain fatty acids and $\omega 3$ fatty acids.

* * * * *